US011458154B2

(12) United States Patent
Polymeropoulos et al.

(10) Patent No.: US 11,458,154 B2
(45) Date of Patent: Oct. 4, 2022

(54) TREATMENT OF CYR61- AND VEGF-MEDIATED CONDITIONS

(71) Applicant: VANDA PHARMACEUTICALS INC., Washington, DC (US)

(72) Inventors: Mihael H. Polymeropoulos, Potomac, MD (US); Louis William Licamele, Potomac, MD (US); Christian Lavedan, Potomac, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 579 days.

(21) Appl. No.: 14/917,098

(22) PCT Filed: Sep. 4, 2014

(86) PCT No.: PCT/US2014/054018
§ 371 (c)(1),
(2) Date: Mar. 7, 2016

(87) PCT Pub. No.: WO2015/035002
PCT Pub. Date: Mar. 12, 2015

(65) Prior Publication Data
US 2016/0213696 A1     Jul. 28, 2016

Related U.S. Application Data

(60) Provisional application No. 61/874,966, filed on Sep. 6, 2013.

(51) Int. Cl.
| | | |
|---|---|---|
| *A61K 31/704* | (2006.01) | |
| *A61K 31/40* | (2006.01) | |
| *A61K 31/405* | (2006.01) | |
| *A61K 31/22* | (2006.01) | |
| *A61K 31/44* | (2006.01) | |
| *A61K 31/505* | (2006.01) | |
| *A61K 31/47* | (2006.01) | |
| *A61K 31/136* | (2006.01) | |
| *A61K 31/365* | (2006.01) | |
| *A61K 31/366* | (2006.01) | |
| *A61K 31/351* | (2006.01) | |
| *A61K 9/00* | (2006.01) | |

(52) U.S. Cl.
CPC .......... *A61K 31/704* (2013.01); *A61K 9/0019* (2013.01); *A61K 9/0053* (2013.01); *A61K 31/136* (2013.01); *A61K 31/22* (2013.01); *A61K 31/351* (2013.01); *A61K 31/365* (2013.01); *A61K 31/366* (2013.01); *A61K 31/40* (2013.01); *A61K 31/405* (2013.01); *A61K 31/44* (2013.01); *A61K 31/47* (2013.01); *A61K 31/505* (2013.01)

(58) Field of Classification Search
CPC .. A61K 31/704; A61K 31/351; A61K 31/136; A61K 31/22; A61K 31/365; A61K 31/366; A61K 31/40; A61K 31/405; A61K 31/44; A61K 31/47; A61K 31/505
See application file for complete search history.

(56) References Cited

U.S. PATENT DOCUMENTS

| | | |
|---|---|---|
| 10,208,007 B2 | 2/2019 | Kapulnik et al. |
| 2003/0065020 A1 | 4/2003 | Gale et al. |
| 2010/0034749 A1* | 2/2010 | Schulze ............... A61K 9/0019 424/9.6 |

FOREIGN PATENT DOCUMENTS

| | | |
|---|---|---|
| JP | 2004512278 A | 4/2004 |
| JP | 2009501707 A | 1/2009 |
| NO | 92/07866 A1 | 5/1992 |
| WO | 2008044339 A1 | 4/2008 |
| WO | 2013/138343 A1 | 9/2013 |

OTHER PUBLICATIONS

Gaudana, R. et al., The AAPS Journal, "Ocular Drug Delivery", Sep. 2010, vol. 12, No. 3, pp. 348-360 (Year: 2010).*
You, J.-J. et al., Investigative Ophthalmology & Visual Science, "Cysteine-rich 61, a Member of the CCN Family, as a Factor Involved in the Pathogenesis of Proliferative Diabetic Retinopathy", Jul. 2009, vol. 50, No. 7, pp. 3447-3455 (Year: 2009).*
Zhang, X. et al., Graefes Arch Clin Exp Ophthalmol, "Cysteine-rich 61 (CYR61) is up-regulated in proliferative diabetic retinopathy", 2012, vol. 250, pp. 661-668 (Year: 2012).*
Babic et al., "CYR61, a product of a growth factor-inducible immediate early gene, promotes angiogenesis and tumor growth," Proc Natl Acad Sci USA. 95:6355-60 (1998).
Chen et al., "Atorvastatin reduces vascular endothelial growth factor (VEGF) expression in human non-small cell lung carcinomas (NSCLCs) via inhibition of reactive oxygen species (ROS) production," Molecular Oncology. 6:62-72 (012).
Database Biosis, Biosciences Information Service, Jul. 2013, Fu Peng et al., "Atorvastatin Inhibits Cyr61 Expression in Cultured Rat Vascular Smooth Muscle Cells," Database accession No. PREV201400191441, abstract.
Duyndam et al., "Cisplatin and doxorubicin repress Vascular Endothelial Growth Factor expression and differentially down-regulate Hypoxia-inducible Factor I activity in human ovarian cancer cells," Biochemical Pharmacology. 74:191-201 (2007).

(Continued)

*Primary Examiner* — Bahar Craigo
(74) *Attorney, Agent, or Firm* — Hoffman Warnick LLC

(57) ABSTRACT

The invention relates generally to the treatment of CYR61- and VEGF-mediated conditions and, more particularly to the treatment of such conditions by administering to an individual a CYR61 downregulator. In one embodiment, the invention provides a method of treating a CYR61-mediated condition in an individual in need of such treatment, the method comprising: administering to the individual an effective amount of at least one CYR61 downregulator (CYR61DR), wherein the effective amount is an amount sufficient to decrease expression of the CYR61 gene in the individual.

10 Claims, No Drawings

(56) References Cited

OTHER PUBLICATIONS

Li et al., "Systemic administration of HMG-CoA inhibitor protects the blood-retinal barrier and ameliorates retinal inflammation in type 2 diabetes," Experimental Eye Research. 89:71-8 (2009).

Takeshi et al., "Safe and Effective Polymeric-Doxorubicin Conjugate Nanoparticles for Prolonged Antiangiogenic Activity in the Eye," May 8, 2012. Retrieved from the Internet: http://www.abstractonline.com/Plan/ViewAbstract.aspx?mID=2866&sKey=ebc9c74c-9211-43d0-9d5c-060396c9ca9a&cKey=33638dc5-1717-4e08-8287-5344c389580c&mKey-{F05CE029-9BF8-4E7C-B48E-9FF7711D4A0E}.

You et al., "Cysteine-riche 61, a Member of the CCN Family, as a Factor Involved in the Pathogenesis of Proliferative Diabetic Retinopathy," Investigative Ophthalmology & Visual Science—IOVS, Association for Research In Vision and Ophthalmology. 50(7):3447-55 (2009).

International Search Report and Written Opinion for PCT/US2014/054018, dated Nov. 28, 2014, 16 pages.

Crockett et al., "Statins are associated with reduced use of steroids in inflammatory bowel disease: A retrospective cohort study", Inflamm. Bowel Dis. 18(6): 1048-1056 (2012).

Hortobagyi, "Anthracyclines in the treatment of cancer", Drugs 54(S4): 1-7 (1997).

Menendez et al., "The angiogenic factor CYR61 in breast cancer: Molecular pathology and therapeutic perspectives", Endrocine-related Cancer 10:141-152 (2003).

Fromique et al., "CYR61 downregulation reduces osteosarcoma cell invasion, migration and metastasis", J. Bone. Miner. Res. 26(7): 1583-1542 (2011).

De Jong et al., "Use of statins is associated with an increased risk of rheumatoid arthritis," Ann. Rheum. Dis. 71(5):648-654 (2012).

Cascales et al., "Association of anthracycline-related cardiac histological lesions with NADPH oxidase functional polymorphisms," Oncologist 18(4): 446-463 (2013).

Wang et al., "EphA2 targeted doxorubicin stealth liposomes as a therapy system for choroidial neovascularization in rats", Investigative Ophthalmology & Visual Science, 2012, 53(11), 7348-7357.

Canadian Office Action for Application No. 2,923,557, dated Feb. 17, 2022, 8 pages.

\* cited by examiner

TREATMENT OF CYR61- AND VEGF-MEDIATED CONDITIONS

CROSS-REFERENCE TO RELATED APPLICATIONS

This application claims the benefit of co-pending U.S. Provisional Patent Application Ser. No. 61/874,966, filed 6 Sep. 2013, which is hereby incorporated herein.

BACKGROUND

The gene cystine-rich, angiogenic inducer, 61 (CYR61) is one member of the CCN gene family, which encode cysteine-rich secreted proteins involved with differentiation and cell growth. CYR61 is known, among other things, to mediate cell adhesion and enhance angiogenesis. Individuals with proliferative diabetic retinopathy (PDR) have been shown to have increased levels of TGB-β, which induces CYR61 expression.

You et al. have shown an ability of the CYR61 protein to induce endothelial cell chemotaxis and tube formation as well as a synergetic effect between CYR61 expression and vascular endothelial growth factor (VEGF) expression. More specifically, You et al. observed significant decreases in both CYR61- and VEGF-induced chemotaxis and tube formation upon the introduction of an anti-CYR61 antibody.

SUMMARY

In one embodiment, the invention provides a method of treating a CYR61-mediated condition in an individual in need of such treatment, the method comprising: administering to the individual an effective amount of at least one CYR61 downregulator (CYR61DR), wherein the effective amount is an amount sufficient to decrease expression of the CYR61 gene in the individual, in particular, though not necessarily, wherein such CYR61DR decreases transcription by at least about 1½-fold.

In another embodiment, the invention provides a method of treating a VEGF-mediated condition in an individual in need of such treatment, the method comprising: administering to the individual an effective amount of at least one CYR61 downregulator (CYR61DR), wherein the effective amount is an amount sufficient to decrease expression of both the CYR61 gene and the VEGF gene in the individual, in particular, though not necessarily, wherein such CYR61DR decreases transcription by at least about 2-fold.

DETAILED DESCRIPTION

Applicants have unexpectedly discovered that members of two known classes of compounds—anthracyclines and statins—are capable of downregulating expression of the CYR61 gene, making them useful in treating CYR61-mediated conditions. In addition, the synergetic effect of CYR61 expression and VEGF expression makes these compounds similarly useful in the treatment of VEGF-mediated conditions.

Typically, in the practice of this invention, CYR61 gene expression is down regulated at least about 1½-fold, e.g., 2-fold, i.e., the amount of CYR61 mRNA is at least about 1½ fold less (e.g., 2-fold less) in treated cells than in untreated cells.

In a study leading to embodiments of the invention, a human retinal pigment epithelial cell line (ARPE-19/HPV16) was separately treated with an anthracycline (doxorubicin or daunorubicin), a statin (simvastatin or lovastatin), or vehicle for 24 hours and gene expression for 22,238 probe sets covering 12,490 genes was generated using an Affymetrix instrument. The effects of these compounds on the expression of CYR61 are shown below in Table 1.

TABLE 1

| | | | CYR61 Downregulation | | | |
|---|---|---|---|---|---|---|
| Probe | Rank | amplitude | CYR61DR | conc. | Vehicle | Fold |
| 210764_s_at | 22272 | −1.92489 | Doxorubicin HCl | 10 uM | water | −52.25522567 |
| 201289_at | 22282 | −1.96653 | Doxorubicin HCl | 10 uM | water | −118.510009 |
| 201289_at | 22255 | −1.37773 | Simvastatin | 10 uM | DMSO | −5.428077844 |
| 210764_s_at | 22262 | −1.3931 | Simvastatin | 10 uM | DMSO | −5.590871643 |
| 210764_s_at | 22239 | −1.8272 | Daunorubicin HCl | 10 uM | water | −22.14814815 |
| 201289_at | 22278 | −1.92127 | Daunorubicin HCl | 10 uM | water | −49.80655405 |
| 210764_s_at | 22264 | −1.29662 | Lovastatin | 10 uM | Ethanol | −4.686826466 |
| 201289_at | 22271 | −1.41167 | Lovastatin | 10 uM | Ethanol | −5.798905376 |
| 210764_s_at | 22267 | −1.87549 | Idarubicin HCl | 10 uM | Methanol | −31.12593366 |
| 201289_at | 22273 | −1.89929 | Idarubicin HCl | 10 uM | Methanol | −38.71800218 |

As can be seen from Table 1, anthracyclines and statins are capable of significant downregulation of CYR61. Within these results, anthracycline downregulation is approximately an order of magnitude or more greater than statin downregulation. Nevertheless, the differences in potential side effects and drug interactions, as well as the extent of CYR61 downregulation desired, make either or both classes of compounds desirable in some circumstances.

Anthracyclines suitable for use according to embodiments of the invention include, for example, doxorubicin, daunorubicin, epirubicin, idarubicin, valrubicin, and mitoxantrone. Statins suitable for use according to embodiments of the invention include, for example, simvastatin, pravastatin, fluvastatin, atrovastatin, cerivastatin, lovastatin, mevastatin, pitavastatin, and rosuvastatin.

According to some embodiments of the invention, one or more anthracycline and/or one or more statin may be administered to an individual in an amount sufficient to affect downregulation of CYR61 and/or VEGF. For example, in one embodiment, an individual may be administered doxorubicin, daunorubicin, or both. In another embodiment, an individual may be administered doxorubicin, a statin, or both.

Conditions that may be treated with one or more CYR61DR include those conditions involving neovascularization and/or inflammation, including, for example, proliferative diabetic retinopathy, neovascular glaucoma, macular degeneration, inflammatory neovascularization, Crohn's disease, ulcerative colitis, retinal neovascularization, retinal vascular disorders, tumor vascularization, cancer angiogenesis, metastasis, rheumatoid arthritis, and fibrosis.

CYR61DRs may be administered to the individual to be treated in the form of a pharmaceutical composition. Pharmaceutical compositions to be used according to various embodiments of the invention comprise a therapeutically effective amount of CYR61DRs or an active metabolite of a CYR61DR, or a pharmaceutically acceptable salt or other form (e.g., a solvate) thereof, together with one or more pharmaceutically acceptable excipients or carriers. The phrase "pharmaceutical composition" refers to a composition suitable for administration in medical use. It should be appreciated that the determinations of proper dosage forms, dosage amounts, and routes of administration for a particular patient are within the level of ordinary skill in the pharmaceutical and medical arts.

Administration may be oral but other routes of administration may also be employed, e.g., intravitreal, parenteral, nasal, buccal, transdermal, sublingual, intramuscular, intravenous, rectal, vaginal, etc. Solid dosage forms for oral administration include capsules, tablets, pills, powders, and granules. In such solid dosage forms, the compound is admixed with at least one inert pharmaceutically-acceptable excipient such as (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, drages, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Solid compositions for oral administration can be formulated in a unit dosage form, each dosage containing from about 1 mg to about 500 mg of active ingredient. The term "unit dosage form" refers to physically discrete units suitable as unitary dosages for human subjects and other mammals, each unit containing a predetermined quantity of active ingredient calculated to produce the desired effect over the course of a treatment period, in association with the required pharmaceutical carrier. CYR61DRs can be formulated, e.g., in a unit dosage form that is a capsule having 1-500 mg of active in addition to excipients.

Liquid dosage forms for oral administration include pharmaceutically-acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

In some embodiments of the invention, CYR61DRs are provided in a liquid form and administered to an individual intravitreally.

While this invention has been described in conjunction with the specific embodiments outlined above, it is evident that many alternatives, modifications and variations will be apparent to those skilled in the art or are otherwise intended to be embraced. Accordingly, the embodiments of the invention as set forth above are intended to be illustrative, not limiting. Various changes may be made without departing from the spirit and scope of the invention as defined in the following claims. All patents, patent application, scientific articles and other published documents cited herein are hereby incorporated in their entirety for the substance of their disclosures.

What is claimed is:

1. A method of treating a patient diagnosed with proliferative diabetic retinopathy (PDR) and having increased expression of the CYR61 gene as compared to the expression expected in an individual without PDR, the method comprising:
   orally administering to the patient an amount of at least one anthracycline effective to decrease expression of the CYR61 gene in the patient by at least about 2-fold.

2. The method of claim 1, wherein the at least one anthracycline is selected from a group consisting of: doxorubicin, daunorubicin, epirubicin, idarubicin, valrubicin, and mitoxantrone.

3. The method of claim 1, wherein the patient has increased levels of TGB-β.

4. A method of treating an individual having a CYR61-mediated condition and increased expression of the CYR61 gene as compared to the expression expected in an individual without a CYR61-mediated condition, the method comprising:
   orally administering to the individual an amount of at least one anthracycline effective to decrease expression of the CYR61 gene in the individual by at least about 2-fold,
   wherein the CYR61-mediate condition is selected from a group consisting of: proliferative diabetic retinopathy, neovascular glaucoma, macular degeneration, inflammatory neovascularization, Crohn's disease, ulcerative colitis, retinal neovascularization, retinal vascular disorders, tumor vascularization, cancer angiogenesis, metastasis, rheumatoid arthritis, and fibrosis; and
   the at least one anthracycline is selected from a group consisting of: doxorubicin, daunorubicin, epirubicin, idarubicin, valrubicin, and mitoxantrone.

5. The method of claim 4,
   wherein the CYR61-mediated condition is selected from a group consisting of:
   neovascular glaucoma, macular degeneration, inflammatory neovascularization, Crohn' s disease, ulcerative colitis, retinal neovascularization, retinal vascular disorders, tumor vascularization, cancer angiogenesis, metastasis, rheumatoid arthritis, and fibrosis.

6. In a method of treating an individual having a CYR61-mediated condition, the improvement comprising:
   selecting for treatment an individual exhibiting increased expression of the CYR61 gene, as compared to an individual not having the CYR-mediated condition; and
   administering to the individual having the CYR61-mediated condition an amount of at least one anthracycline effective to decrease expression of the CYR61 gene by at least about 2-fold,
   wherein the CYR61-mediated condition is selected from a group consisting of: neovascular glaucoma, macular degeneration, inflammatory neovascularization, Crohn's disease, ulcerative colitis, retinal neovascularization, retinal vascular disorders, tumor vascularization, cancer angiogenesis, metastasis, rheumatoid arthritis, and fibrosis.

7. The improvement of claim 6, wherein the at least one anthracycline is selected from a group consisting of: doxorubicin, daunorubicin, epirubicin, idarubicin, valrubicin, and mitoxantrone.

8. The improvement of claim 6, wherein administering includes intravitreally administering.

9. The improvement of claim 6, wherein administering includes orally administering.

10. The improvement of claim 6, wherein administering includes administering intravenously.

* * * * *